United States Patent [19]

Singhal et al.

[11] Patent Number: 4,603,408
[45] Date of Patent: Jul. 29, 1986

[54] SYNTHESIS OF ARBITRARY BROADBAND SIGNALS FOR A PARAMETRIC ARRAY

[75] Inventors: Sharad Singhal, Plainfield, N.J.; John G. Zornig, New Haven, Conn.

[73] Assignee: The United States of America as represented by the Secretary of the Navy, Washington, D.C.

[21] Appl. No.: 516,013

[22] Filed: Jul. 21, 1983

[51] Int. Cl.⁴ .............................................. G01S 7/52
[52] U.S. Cl. .................................... 367/92; 367/95; 367/137
[58] Field of Search ........................... 367/92, 95, 137

[56] References Cited

U.S. PATENT DOCUMENTS 3,614,719 10/1971 Treacy .................................. 367/95

Primary Examiner—Richard A. Farley
Attorney, Agent, or Firm—Robert F. Beers; Arthur A. McGill; Prithvi C. Lall

[57] ABSTRACT

A method for synthesizing arbitrary broadband signals for a parametric array which computes the input waveform needed to a parametric array source to obtain a received signal of a prescribed waveform. The method uses Fourier transform and the inverse transform of digitized received signal in order to make computation in either the frequency domain or the time domain depending upon the computational simplicity in a particular domain. The method uses a iterative process to obtain the received signal very close to the received signal of the desired waveform.

6 Claims, 15 Drawing Figures

SYNTHESIS OF ARBITRARY BROADBAND SIGNALS FOR A PARAMETRIC ARRAY

The invention described herein may be manufactured and used by or for the Government of the United States of America for governmental purposes without the payment of any royalties thereon or therefor.

BACKGROUND OF THE INVENTION (1) Field of the Invention

Subject invention is related the field of acoustic parametric arrays and more particularly to a new method of synthesizing arbitrary broadband signals for a parametric array.

(2) Description of the Prior Art

In its simplest form, an acoustic parametric array includes a transducer transmitting a signal composed of at least two discrete frequencies, hereinafter called "primaries". As the primaries propagate in a medium such as water, as result of medium nonlinearities, sum-and-difference frequencies, hereinafter called "secondaries" are generated along the length of the primaries. At some distance, the higher frequency sounds are absorbed, leaving the difference frequency secondary as the resultant. Because the secondary is generated along the length of the primary beams, the parametric array behaves as a virtual endfire array whose length depends upon the absorption of the primaries in the medium, and which is characterized by narrow, nearly side-lobe free beams at relatively low frequency and over broad frequency bands.

Westervelt in his article; "Parametric Acoustic Array", J. Acoust. Soc. Am. 35, 535–537 (1963); first described an acoustic parametric array. A large number of researchers have studied its properties and operation which are now fairly well understood. Most of this work on parametric arrays has been directed towards narrow-band sources in which two discrete primaries interact to form a secondary with a single difference frequency as the secondary. Berktay in his article; "Possible Exploitation of Nonlinear Acoustics in Underwater Transmitting Applications", Journal of Sound Vib. 2, 435–461 (1965); first discussed the possibility of obtaining a broadband secondary signal by the use of pulsed primary signals. His assumptions limited his results to the case in which small signal absorption limited the array length to be in the nearfield of the transducer. Subsequently, a number of researchers have done both theoretical and experimental work and considered cases in which nonlinear absorption and farfield generation takes place. However, most of the previous work has been concentrated on trying to determine the secondary pressure for a given primary. The problem of finding the transmit signal which, when applied to the projector (transmitter) would result in a received waveform by the hydrophone (receiver) that is closed to a given shape or waveform has not been so far addressed. Because of the importance of low frequency directed beam in the areas of communication and oil exploration using a profile of the bottom of the ocean, it is desirable to have a technique for obtaining a low frequency directed beam pattern having a particular signal characteristics which is obtained by applying the necessary primaries.

SUMMARY OF THE INVENTION

Arbitrary broadband signals of a parametric array are obtained by an adaptive signal synthesis technique which uses the Fourier transform of the digitized received signal waveform as a basis for modifying the source signal recursively until the received waveform is close to a given desired waveform shape. The method avoids completely the numerical integrations normally associated with parametric source signal design and converges to a satisfactory result within a few iterations. Consequently, it is a simple and quick technique for obtaining a low frequency directed beam which can be used on line.

The novel technique of subject invention includes an iterative process which starts with an approximate value of the input or transmit signal and uses Fourier transforms and inverse transforms to make calculations in the frequency and time domain to simplify mathematical computations. The method yields a value of the received or output signal which is obtained by starting with an approximate transmit signal and after a few iterations as taught by subject technique eventually leads to a received or output signal which is very close to the received signal of a given desired waveform.

An object of subject technique is to have a broadband signals of low frequency for a parametric array.

Another object of subject invention is to obtain a low frequency directed signals for a parametric array.

Still another object of subject invention is to have a technique which produces a signal of desired characteristics using frequencies which can be easily calculated using subject technique.

Still another object of subject invention is to provide an arbitrary broadband signal source wherein the output of such a source is predetermined.

Other objects, advantages and novel features of the invention may become apparent from the following detailed description of the invention when considered in conjunction with the accompanying drawings wherein:

DESCRIPTION OF A PREFERRED EMBODIMENT

Figure 1:
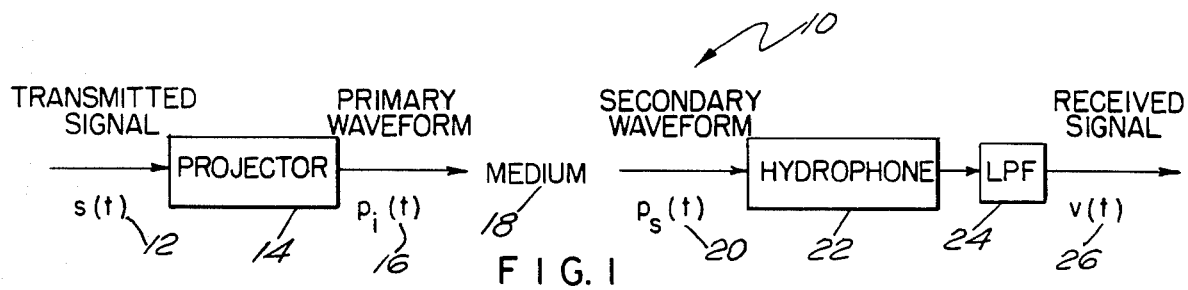
FIG. 1 is a schematic representation of the technique according to the teachings of subject invention.

The technique of synthesizing arbitrary broadband signals for a parametric array according to the teachings of subject invention is accomplished by using Fourier transform of the digitized received waveform signal as a basis for modifying the source signal recursively until the received signal waveform is close to the desired signal waveform. FIG. 1 schematically represents a typical wide band parametric array system 10. A signal s(t) represented by 12 is applied to a projector or transmitter 14 which transmits a primary waveform 16 shown as $p_i(t)$. As the primary propagates in the medium 18, the secondary waveform $p_s(t)$ represented by 20 is generated and is received by hydrophone or receiver 22. The output of hydrophone 22 is filtered by low pass filter (LPF) 24 to filter any high frequency components to obtain received signal v(t) represented by 26. It should be noted that the transmit, s(t), and received v(t) signals may be of different waveshapes other than the primary and secondary waveforms respectively because of the transmitter and hydrophone frequency response characteristics.

If a primary source (projector or transmitter) is located at the origin; r being the position vector of the observation point, r' being the position vector of the secondary source so that $\xi = |r - r'|$, $c_0$ being the velocity of sound in the medium, $\rho_0$ being the ambient fluid density, $\omega$ being angular secondary frequency; as indicated in the article: "Synthesis of Arbitrary Broadband Signals for a Parametric Array" by Singhal & Zornig, J. Acoustic Soc. Am, 72(1), July 1982, pp. 238–244, the observed secondary pressure field $p_s(r,t)$ or pressure wave at the hydrophone or the observation point is given by:

$$P_s(\underline{r},t) = \frac{\rho_0}{4\pi} \int\int\int \frac{d^3 \underline{r}'}{\xi} \frac{\partial}{\partial t}\left[ q\left(\underline{r}', t - \frac{\xi}{c_0}\right) \right], \quad (1)$$

where acoustic source density, (r',t) is:

$$q(\underline{r}',t) = \frac{\beta}{\rho_0^2 c_0^4} \frac{\partial}{\partial t} p_i^2(\underline{r}',t) \quad (2)$$

$\beta$ being the nonlinearity parameter having a value of about 3.5 for water and the integration is carried over all r' where there is significant source density.

It is assumed in this analysis that the primary is a constant amplitude plane wave with no dispersion and attenuation. The effects on the primary of linear or nonlinear attenuation, dispersion or spreading and the finite aperture of the projector or transmitter are included in the form of an ad-hoc taper function T (r',$\omega$) which is dependent upon the mechanism of attenuation, the projector size and shape, the primary frequencies and amplitude.

We want to find $p_i(r',t)$ from a given waveform of $p_s(r,t)$. However, the integral given by equation (1) cannot be solved exactly because of the geometry, the transmitter (projector) and receiver (hydrophone) characteristics which are unknown, physical constants and the non-linearity of the medium. Closed form evaluation of the integral is not possible. However, the problem can be solved in two steps, i.e., (a) evaluation of the correction due to nonlinearity and (b) make an estimation of the integral. Steps (a) and (b) are performed using Fourier transforms and inverse transforms to go from the time domain to the frequency domain and vice versa in order to make the computations simpler than they would be otherwise. Steps (a) and (b) are performed iteratively and iterations are carried on until the estimated received signal is very close to the desired waveform.

Fourier transforming equation (1), we have:

$$\underline{F_s}(\underline{r}',\omega) = \frac{\rho_0}{4\pi} \int\int\int \frac{d^3 \underline{r}'}{\xi} j\omega e^{-j\omega\xi/c_0} \underline{Q}(\underline{r}',\omega), \quad (3)$$

where $$Q(r',\omega) = F[q(r',t)]. \quad (4)$$

If we limit our attention to the secondary signals which can be generated by the amplitude modulated primaries, the transmit signal can be written as:

$$s(t) = Re[b(t)e^{j\omega_0 t}], \quad (5)$$

where b(t) is the envelope, and $\omega_0$ is the angular primary center (carrier) frequency.

As shown in the article by Singhal and Zornig cited above, if the receiver transfer function is R($\omega$), we have F(r,$\omega$), the received signal transform, given by:

$$F(r,\omega) = F_s(r,\omega) \cdot R(\omega) \quad (6)$$

and thus $$A(\omega) = F(r,\omega) \cdot G(r,\omega), \quad (7)$$

where $$\underline{G}(\underline{r}',\omega) = \frac{8\pi\rho_0 c_0^4}{(j\omega)^2 \beta \underline{R}(\omega)} \left( \int\int\int \frac{d^3 \underline{r}'}{\xi} \exp\left(\frac{-j\omega\xi}{c_0}\right) \underline{T}(\underline{r}',\omega) \times \right.$$

$$\left\{ \int_0^{t_{max}} d\tau \int_0^{t_{max}} d\gamma h(\tau)h(\gamma)\cos\omega_0(\gamma - \tau) \times \right.$$

$$\left.\left. \exp\left[-j\omega\left(\frac{r'}{c_0} + \gamma\right)\right] \right\} \right)^{-1} \quad (8)$$

and $$\underline{A}(\omega) = \int_{-\infty}^{\infty} du \underline{B}(u)\underline{B}(\omega - u) = F[b^2(t)]. \quad (9)$$

and $$\underline{B}(\omega) = F[b(t)]. \quad (10)$$

This reduces the problem to one of computing G(r,$\omega$) which is dependent on the geometry, the transmitter and receiver characteristics, physical constants, and the center of frequency and computing the required envelope b(t) from A($\omega$), the transform of the squared envelope.

As mentioned earlier, T(r,$\omega$), the ad-hoc taper function, to account for the attenuation and dispersion of the primary can be fairly complicated in practical cases and its exact form depends upon the mechanism of attenuation, the projector (transmitter) size and shape and the frequencies of the primaries.

It should be further noted that function h(t) represents the transmitter impulse response and appears in the double integral in equation (8) where $\gamma$ and $\tau$ represent the time variable for integration purposes.

Closed form evaluation of $G(r,\omega)$ normally is not possible and the integral has to be evaluated numerically. This involves making a number of approximations and assumptions regarding the taper function and the integration volume. Thus the numerical integration is both computationally cumbersome and approximate. Again $G(r,\omega)$ includes the effect of the transmitter and receiver characteristics, which usually are not known completely, and has to be recomputed for each transmitter or receiver used. However, if the physical situation allows an on-line estimation of $G(r,\omega)$, the numerical integral may be avoided and an algorithm constructed which would allow the synthesis of the required transmit signal for any particular geometry without detailed knowledge of the transmitter or receiver characteristics.

Let $F_d(\omega)$ be the transform of the desired output waveform at a given r (i.e., for a given observation point). Let $G_0(\omega)$ be an initial value [possibly obtained by an approximate evaluation of (8) for the given geometry]. Then the following basic adaptation scheme is used:

(1) Compute $A_i(\omega) = F_d(\omega)G_i(\omega)$
(2) $A_i(\omega)^{-1} \rightarrow b_i^2(t) \rightarrow b_i(t) \xrightarrow{cos\omega_0 t} s_i(t)$
(3) Transmit $s_i(t)$ and obtain the response $v_i(t)$
(4) $v_i(t) \rightarrow F_i(\omega)$
(5) $G_{i+1}(\omega) = k[A_i(\omega)/F_i(\omega)] + (1-k)G_i(\omega)$ and repeat the procedure until $F_i(\omega)$ is close to $F_d(\omega)$. Note that for a given observation point r is fixed and consequently is not variable.

Figure 2:
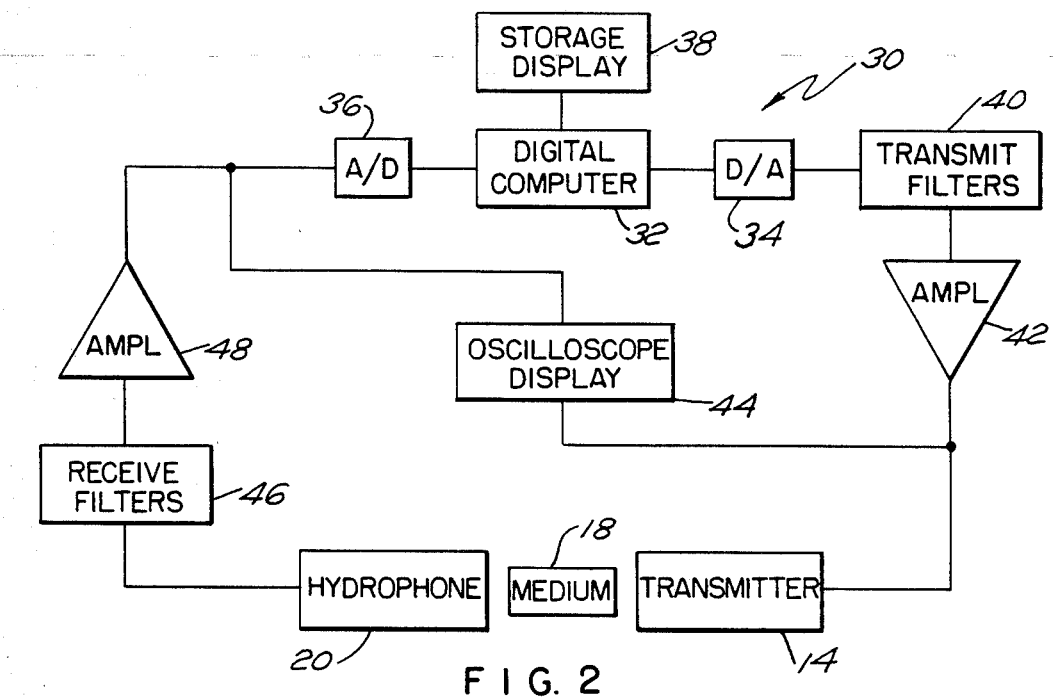
FIG. 2 is a schematic representation of the experimental steps used in subject technique.

The above-mentioned steps are used to go through the iterative process according to the teachings of subject technique. Having made approximations to evaluate $G(r,\omega)$ given equation (8), the Fourier transform of the desired received signal is obtained. Step (1) includes calculation of $A_i(\omega)$ which is the transform of $b_i^2(t)$ where $b_i(t)$ is the envelope of the transmit signal. Step (2) involves taking inverse Fourier transform of $A_i(\omega)$, taking the square root thereof to find $b_i(t)$ and the real part of $b_i(t)$ to obtain $s_i(t)$, the transmit signal $s_i(t)$ is transmitted through the medium 18 as shown in FIGS. 1 and 2 and received signal $v_i(t)$ is obtained in step (3). The value of $F_i(\omega)$ is computed from $v_i(t)$ in step (4). The new value of $F_i(\omega)$ is used to find new value of $G_i(\omega)$ where k is recursive filter coefficient with a value less than 1.

$A_i(\omega)$ is inverse Fourier transformed to obtain b (t). Since static pressures are not transmitted in the medium, the system is high pass in nature. Thus the estimation procedure cannot obtain the dc term in $A_i(\omega)$ which is needed so that $b_i^2(t)$ is positive for all t and some form of dc restoration is required. We add in the envelope of the negative going peaks in $b_i^2(t)$ to it to make b (t)>0 and take the square root to obtain $b_i(t)$. All values of $b_i(t)$ are taken to be positive. Any phase reversals are included in $G(\omega)$ during the adaptation process. $b_i(t)$ is then multiplied by the carrier cos ($\omega_0 t$) to obtain the transmit signal $s_i(t)$.

Having transmitted the synthesized signal we need to measure its response and update $G(\omega)$. Measurement of the response involves making an estimate of the received waveform in the presence of noise. Various methods are available to do this which take both signal and noise considerations into account. However, if the signal-to-noise ratio is sufficiently large a simple averaging of a series of responses is enough to give good results. $G(\omega)$ is updated by a recursive filter as in step (5). For the filter to converge is required to be a positive number with magnitude less than one. The inverse filtering operation implied in step (5) does not cause problems with zeros in the denominator, as wideband noise is present in any practical setup and it does not allow $F_i(\omega)$ to become zero at any frequency of interest.

The experimental setup based upon the teachings of subject invention is schematically shown as 30 in FIG. 2. It includes a digital computer 32 such as Digital Scientific META-4 or PDP11/23 by DEC using FORTRAN IV. Computer 32 is used as the starting point in the process. It should be noted that computer 32 is a general purpose computer with a series of programs stored therein to (1) put in all the constants and find the Fourier transform $f_d(\omega)$ from the value desired signals; (2) to make an initial estimate of $G_i(\omega)$ and compute $A_i(\omega)$ and $s_i(t)$; (3) transmit after changing the digitized signal to analog form by D/A converter 34 and receive the receiving signal after being converted from analog-to-digital form by A/D converter 36; and compute a new value of $G(\omega)$. Computer 32 thus sends a transmit signal to D/A converter 34, the output of which is fed to transmit filter 40. The output of filter 40 is amplified by amplifier 42 and the amplified signal is then fed to oscilloscope 44 for display and is also applied to projector or transmitter 14. The output 16 of the transmitter 14 is then transmitted in the medium 18 such as water which has both linear and nonlinear characteristics. The transmitted signal is received by hydrophone or receiver 20, the output of which is filtered by receive filters 46 and amplified by amplifier 48. The amplified output is stored on oscilloscope 44 and digitized by A/D converter 36 and is stored as the received signal 26 by the computer 32 and displayed in storage display unit 38. The computer recomputes a new value of $G(\omega)$ and this iterative process is repeated until the received signal reaches the given desired waveform for the known input signal.

Figure 3:
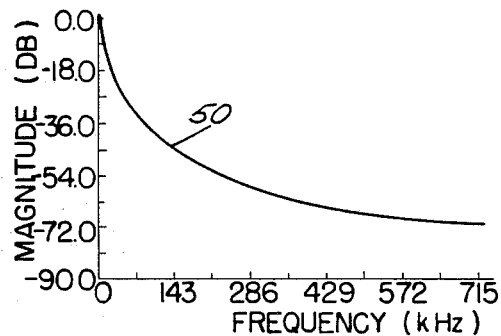
FIGS. 3 and 4 respectively show the magnitude and phase respectively of a function $G(\omega)$ used in the computation in one of the specific examples of subject technique.
Figure 4:
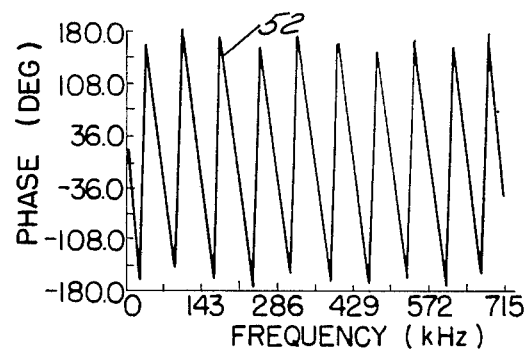

FIGS. 3 and 4 represent the magnitude and phase respectively of the function $G(\omega)$ which is the first approximated value of the integral given by equation (8) under simplified assumptions as described in the above-cited article by Singhal and Zornig. It should be noted that the magnitude of $G(\omega)$ starts at a high value at low frequencies and tapers off as the frequency goes up as shown by curve 50. The phase $G(\omega)$ is shown as curve 52 in FIG. 4.

Figure 5:
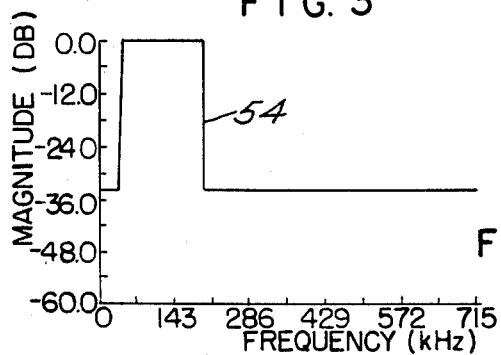
FIG. 5 is a graphical representation of one of the desired signal specifications.
Figure 6:
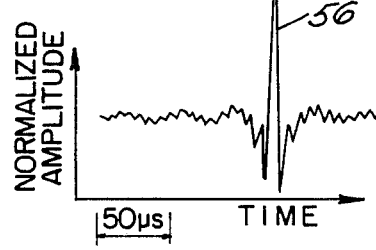
FIG. 6 is a time-amplitude signal representation corresponding to the specification of the signal in FIG. 5.
Figure 7:
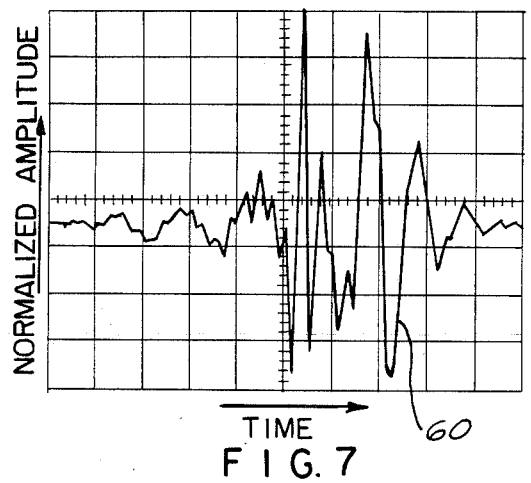
FIG. 7 is a plot of the computed initial received signal with 180 microsecond (1 $\mu sec = 10^{-6}$ second) full scale.

FIGS. 5 and 6 are correlated in that curve 54 of FIG. 5 represents the Fourier transform of the specification (zero phase) of the desired signal as shown by curve 56 of FIG. 6 wherein the amplitude is plotted against time with time interval of 50 sec as shown. Curve 60 of FIG. 7 represents the form of the initial received signal as computed by using an approximate value of $G(\omega)$ whereas curve 62 represents the value of the computed received signal after four iterations as outlined in the technique of subject invention. The similarity of curve 62 of FIG. 8 to the curve 56 of FIG. 6 which is the desired waveform of the received signal is quite evident indicating that four iterations are sufficient to obtain a received signal which is very close in waveform to the given received signal with a particular waveform.

Figure 8:
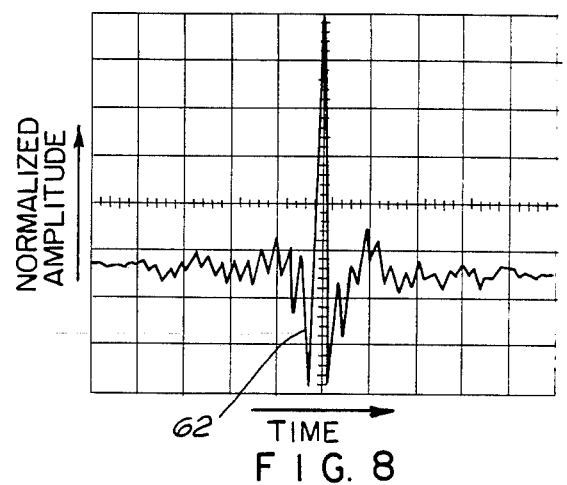
FIG. 8 is a graphical representation of the received signal after four iterations.
Figure 9:
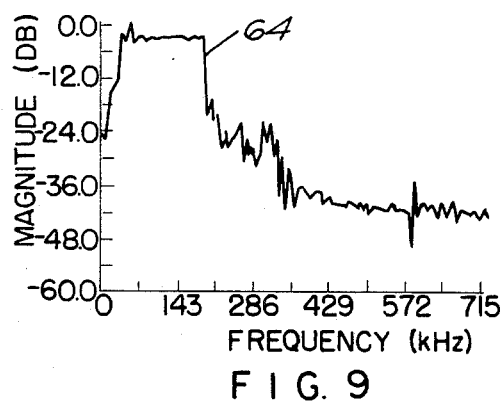
FIGS. 9 and 10 represent the magnitude and phase respectively of the Fourier transform of the received signal as shown in FIG. 8.
Figure 10:
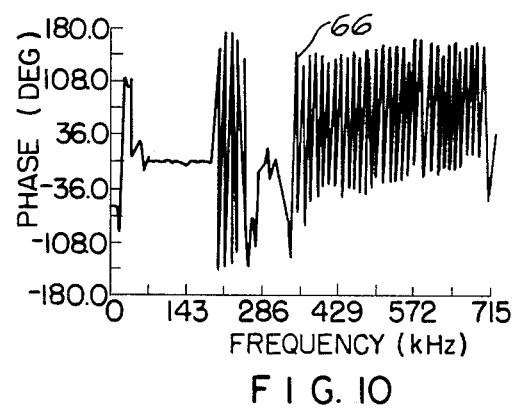

FIGS. 9 and 10 represent the magnitude (curve 64 of FIG. 9) and phase curve 66 of FIG. 10 respectively of the received signal shown by curve 62 of FIG. 8.

The algorithm outlining the steps (1) through (5) was tested on both narrowband and wideband secondaries for both on-axis and off-axis positions of the receiver. Convergence normally took from three to five iterations with the recursive filter coefficient k set to 0.5 when updating G(w).

Figure 11:
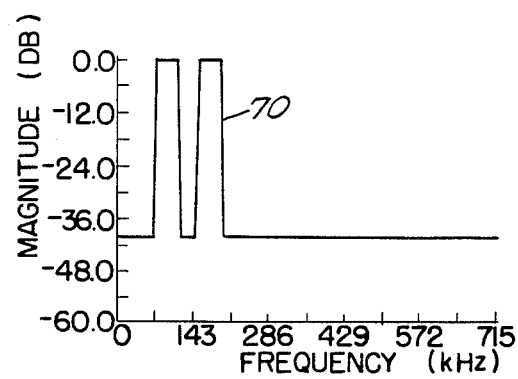
FIG. 11 is a representation of another example of the desired signal of specified magnitude with zero phase.
Figure 12:
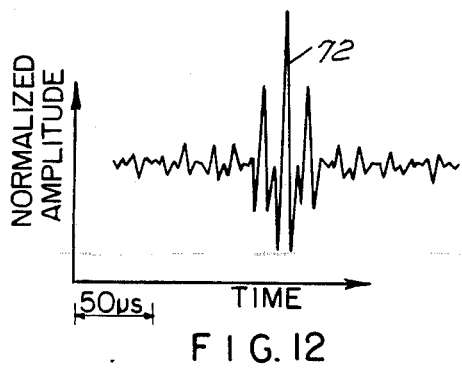
FIG. 12 is a time-amplitude plot signal corresponding to the signal specified in FIG. 11.
Figure 13:
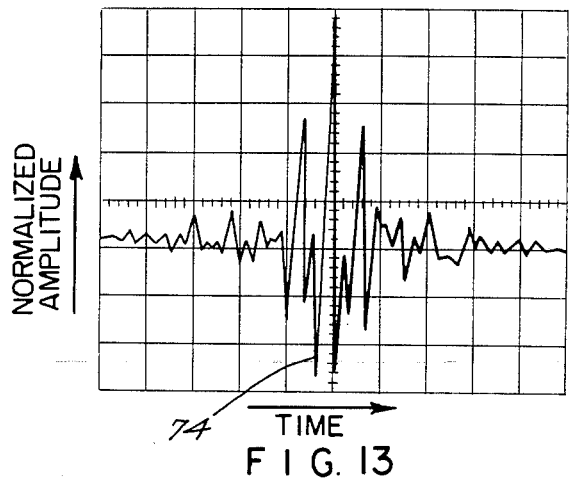
FIG. 13 is the graphical representation of the computed received signals after three iterations with 180 $\mu sec$ full scale.
Figure 14:
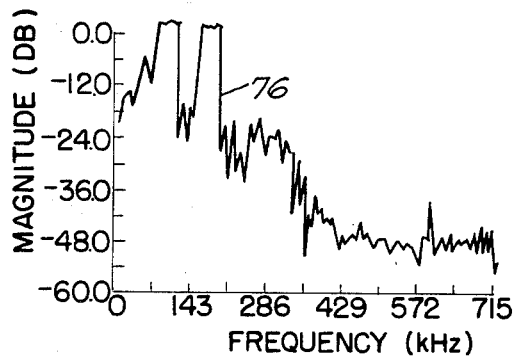
FIGS. 14 and 15 represent the magnitude and phase respectively of the Fourier transform of the received signal of FIG. 13.
Figure 15:
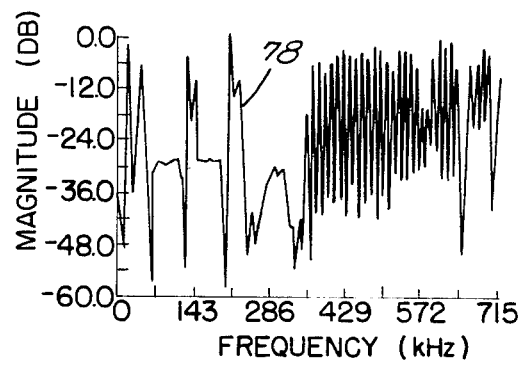

As a different example, another signal with zero phase and magnitude constant over 80–120 kHz and 160–200 kHz as shown by curve 70 of FIG. 11 was tried. The desired signal is shown in FIG. 12 as curve 72 with the appropriate time scale shown therein. The shape of the received signal is shown as curve 74 of FIG. 13 after three iterations according to the teachings of subject invention. Curve 76 of FIG. 14 represents the magnitude of the received signal of FIG. 13 and curve 78 of FIG. 15 represents the phase of the received signal shown by curve 74 of FIG. 13.

It was found out that the algorithm works well with different wideband signals. It was seen to do so as long as the signal-to-noise ratio at the receiver remained at least 15–20 dB. For signal-to-noise ratios less than about 10 dB the algorithm did not converge. This is because the algorithm is sensitive to the phase of the received signal and the poor signal-to-noise ratio results in a phase error large enough to cause the agorithmm to diverge. If this method is to be used for applications in which noise is a problem, appropriate signal techniques would have to be incorporated to ensure a good estimate of the received signal phase.

Briefly stated, the method of synthesizing arbitrary broadband signals for a parametric array includes estimation of the secondary source pressure density integral by approximating the integral and Fourier transforms and inverse Fourier to use an iterative process which after a few iterations gives a received signal which is very close to the given desired waveform of the receive signal. Subject technique thus finds input primary frequencies which when transmitted through the medium gives the received signal very close to the desired waveform.

Obviously, many modifications and variations of the present invention are possible in the light of the above teachings. As an example, a general computer other than Digital Scientific META-4 or PDP 11/23 can be used. Furthermore, a computer language other than FORTRAN IV can be used to execute the algorithm for computations. It is, therefore, to be understood that within the scope of the appended claims the invention may be practiced otherwise than as specifically described.

What is claimed is:

1. A method involving non-linear input-output frequency and amplitude relationships for synthesizing broadband signals similar to a given low frequency signal for a parametric array involving using a general purpose digital computer, a display means, a projector, a hydrophone, an A/D converter, a D/A converter, low pass transmit and receive filters, amplifiers and means for generating high frequencies acting as primaries and forming a difference frequency secondary when traveling through a nonlinear medium, said method includes the steps of:

generating a first value of a function proportional to an integral representing the difference frequency secondary;

obtaining a first value of a computed received signal using said function;

using the first value of the computed received signal to obtain a second value of said function;

obtaining a second value of said function;

obtaining a third value of the computed received signal from the second value of said function;

repeating the above-cited method steps until the computed received signal is similar to the given low frequency signal when displayed on said display means.

2. The method of claim 1 wherein the step of obtaining a first value of a computed receive signal includes computing Fourier and inverse Fourier transforms to simplify computations.

3. The method of claim 2 which further includes the step of filtering high frequency components from transmit and received signals using transmit and receive filters respectively.

4. The method of claim 3 which further includes the step of amplifying filtered transmit and received signals using said amplifiers.

5. The method of synthesizing broadband, low frequency and directed signals for a parametric array using a general purpose digital computer which includes the steps of:

computing a digitized value of a transmit signal from a received signal using said general purpose computer;

converting said digitized value of the transmit signal into analog form thereof using a digital to analog converter;

transmitting the transmit signal in analog form as a transmitted signal using a projector;

receiving said transmitted signal using a hydrophone;

converting said received signal from analog to digital form using an analog to digital converter; and computing a new value of transmit signal from the received signal; and repeating the above steps to obtain a received signal similar to the desired waveform for the received signal.

6. The method of claim 5 which further includes the step of filtering high frequency components from the transmit and received signals.

* * * * *

UNITED STATES PATENT AND TRADEMARK OFFICE
CERTIFICATE OF CORRECTION

PATENT NO. : 4,603,408
DATED : 7/29/86
INVENTOR(S) : John G. Zorning, Sharad Singhal It is certified that error appears in the above-identified patent and that said Letters Patent is hereby corrected as shown below:

Column 1., line 4. insert the following:

The invention identified above is a subject invention under 35 U.S.C. 200, et seq., and the Standard Patent Rights Clause at 37 C.F.R. 401.14 or F.A.R. 52.227-11, which are included among the terms of the above-identified grant/contract award from the Public Health Service/National Institutes of Health.

Signed and Sealed this

Twenty-seventh Day of July, 1999

*Attest:*

Q. TODD DICKINSON

*Attesting Officer*     *Acting Commissioner of Patents and Trademarks*